United States Patent
Channer

(10) Patent No.: US 6,699,432 B2
(45) Date of Patent: Mar. 2, 2004

(54) AIR FRESHENER DEVICE AND METHOD OF FRESHENING AIR

(75) Inventor: Robert Vern Channer, Oxon (GB)

(73) Assignee: Reckitt Benckiser (UK) Limited, Sloughire (GB)

( * ) Notice: Subject to any disclaimer, the term of this patent is extended or adjusted under 35 U.S.C. 154(b) by 0 days.

(21) Appl. No.: 10/122,437

(22) Filed: Apr. 12, 2002

(65) Prior Publication Data

US 2002/0168301 A1 Nov. 14, 2002

Related U.S. Application Data

(63) Continuation of application No. PCT/GB00/03841, filed on Oct. 6, 2000.

(30) Foreign Application Priority Data

Oct. 12, 1999 (GB) ............................................. 9923993

(51) Int. Cl.[7] .................................................. A61L 2/00
(52) U.S. Cl. ............................... 422/5; 422/4; 422/120; 422/122; 422/123
(58) Field of Search ................................ 422/120, 122, 422/123, 4, 5

(56) References Cited

U.S. PATENT DOCUMENTS

| 4,419,326 A | | 12/1983 | Santini | |
|---|---|---|---|---|
| 4,477,414 A | | 10/1984 | Muramoto et al. | |
| 4,878,615 A | * | 11/1989 | Losi | 239/45 |
| 4,913,350 A | * | 4/1990 | Purzycki | 239/44 |
| 5,121,881 A | * | 6/1992 | Lembeck | 239/44 |
| 5,534,229 A | * | 7/1996 | Nomura et al. | 422/123 |
| 5,749,519 A | * | 5/1998 | Miller | 239/44 |
| 5,840,246 A | * | 11/1998 | Hammons et al. | 422/4 |

FOREIGN PATENT DOCUMENTS

| CH | 660 715 A5 | 6/1987 |
|---|---|---|
| EP | 0 501 601 A1 | 9/1992 |
| FR | 2 705 537 A1 | 12/1994 |

* cited by examiner

Primary Examiner—Krisanne Thornton
(74) Attorney, Agent, or Firm—Akin Gump Strauss Hauer & Feld LLP

(57) ABSTRACT

A fragrance emanating device for freshening atmospheric air has (i) a closed container for accommodating a liquid fragrance composition in its interior, (ii) an emanator having a surface open to the ambient air for evaporation of the liquid fragrance composition, and (iii) a conduit linking the emanator surface with the liquid fragrance composition in the interior of the container. The components of the device are so dimensioned that, in use, thermal expansion of air and/or liquid in the container, resulting from an increase in temperature, causes a portion of the fragrance composition to travel along the conduit from the container to the emanator surface, and thermal contraction of the air and/or liquid in the container, resulting from a decrease in temperature, causes air from the atmosphere to enter the container via the conduit. The device enables a fresh supply of fragrance composition to be fed to the emanator surface each day, thereby preventing gradual diminution in the rate of emanation of the fragrance composition with time.

19 Claims, 1 Drawing Sheet

AIR FRESHENER DEVICE AND METHOD OF FRESHENING AIR

CROSS-REFERENCE TO RELATED APPLICATIONS

This application is a continuation of International Patent Application No. PCT/GB00/03841, filed Oct. 6, 2000, which was published in the English language on Apr. 19, 2001 under International Publication No. WO 01/26698 A1, the disclosure of which is incorporated herein by reference.

BACKGROUND OF THE INVENTION

This invention is directed to air freshening devices of the type suitable for use in domestic environments. The invention is further directed to a method for freshening ambient air in such environments.

It is known to provide air freshening devices which slowly release a fragrance into the atmosphere in order to avoid or mask unpleasant odors. Such air freshening devices may comprise a gel-like matrix containing one or more fragrance components. The matrix includes an emanating surface from which the fragrance evaporates on contact with the air. However, such conventional air freshening devices suffer from the disadvantage that the concentration of the fragrance component or components remaining within the matrix decreases with time and a concentration gradient thus forms across the matrix. Thus, as time passes, the emanating surface contains less fragrance and the rate of fragrance emanation decreases. The user of the air freshening device then perceives that the air freshening device is less efficient as time progresses.

An alternative type of air freshening device comprises a liquid in a container provided with a wick into which liquid can be drawn by capillary action. The volatile liquid can evaporate from the exposed end of the wick. As the level of liquid in the container falls, the liquid must travel a greater distance up the wick before it can evaporate. As a result, it is difficult to obtain a uniform release of fragrance over time.

It would be desirable to develop a fragrance emanating system which overcomes the above disadvantages.

BRIEF SUMMARY OF THE INVENTION

Accordingly, the present invention provides a fragrance emanating device for freshening atmospheric air, which device comprises:

(i) a closed container for accommodating a liquid fragrance composition, (ii) an emanator having a surface open to the atmosphere (ambient air) for evaporation of the liquid fragrance composition, and (iii) a conduit linking the container and the emanator surface.

The arrangement of the components of the device is such that, in use, thermal expansion of the air and/or liquid in the container, resulting from an increase in temperature, causes the fragrance composition to travel along the conduit from the container to the emanating surface of the emanator, and thermal contraction of the air and/or liquid in the container, resulting from a decrease in temperature, causes air from the atmosphere to enter the container via the conduit.

Using the air freshening device of the present invention, a fresh supply of the fragrance composition is fed to the emanating surface with each temperature increase and temperature decrease cycle. Thus, there is no gradual diminution in the rate of emanation with time.

In a particularly preferred embodiment, the container includes a base at one end to enable the device to be supported on a level surface and, at its other end, it includes an emanator having a dished emanator surface. The conduit connecting the container and the emanator may be in the form of a dip tube, generally vertically disposed within the interior of the container, and extending between the emanating surface and the base of the container. By suitable selection of the volume of the container, the volume of the conduit and the diameter thereof, it can be ensured that the thermal expansion and contraction occurring with daily changes in the temperature of the air cause fragrance composition to be expelled from the container to the emanating surface and air to be drawn into the container from the atmosphere to replace the expelled fragrance.

If appropriate, the container may be suitably thermally insulated in order to achieve the desired daily range of temperature variation.

In one embodiment of the present invention, the container is only partially filled with the fragrance composition, so that it also contains atmospheric air. In this case, it is primarily the expansion of the air above the surface of the fragrance composition with temperature change which results in the desired expulsion of the fragrance composition from the container. Alternatively, the container may initially be completely filled with fragrance composition, in which case the thermal expansion of the fragrance composition itself provides the driving force for expelling the fragrance composition from the container. Alternatively, the device may be primed by removal of an initial charge of liquid, for example, applying pressure to a flexible container which is full of the fragrance composition. As time passes, air will be drawn into the container and the expansion and contraction of the air will then contribute to the expulsion of fragrance composition in subsequent temperature cycles.

In another embodiment, the driving force is derived from the liquid only. In this case the device includes a reservoir to top up the container with liquid as fragrance composition is removed and a means is provided for removing the air which enters the container from the atmosphere during cooling. The control of liquid flow and air removal may include various valve arrangements.

In one form of this embodiment, the container may include another liquid, in addition to the liquid fragrance composition. This other liquid may be a liquid (such as ethanol) miscible with the liquid fragrance composition or a liquid which is immiscible (such as water or a perfluoroether) with the liquid fragrance composition. This other liquid similarly provides the driving force for expelling the fragrance from the container due to its thermal expansion and contraction.

The container may be formed, for example, of plastic materials, glass, ceramic, pottery or metal, the prime requirement being to contain the liquid fragrance composition and the air in a manner such that expansion can only occur up the dip tube.

The emanator may be formed from a porous material, which may be treated so as to make it hydrophobic or lipophobic, as appropriate. Suitable porous materials include ceramics or earthenware, plastic materials, paper, cellulose wadding, and finely divided mineral particles, such as silica, alumina or carbon. The emanator may be in the form of a flat plate or a film, planar or curviform, and may be wholly formed from the porous material or may be a composite of porous and non-porous materials.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
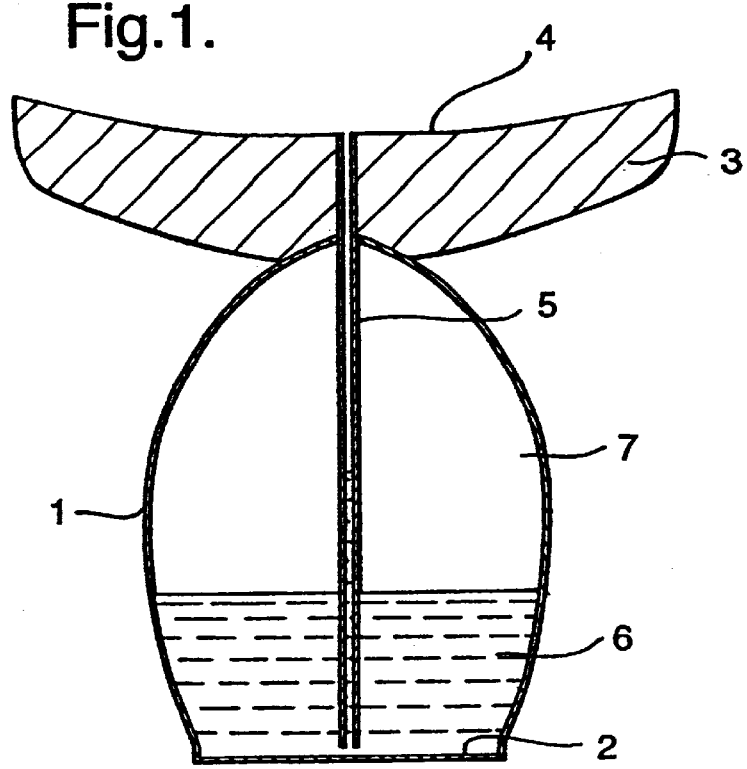
FIG. 1 is a schematic, cross-sectional, side view of a device in accordance with the invention, prior to use.

Referring to FIG. 1, there is shown a closed vessel 1 formed, for example, of a plastic material and having a planar base portion 2. Mounted on the upper portion of the vessel 1 is an emanator 3 having an upper dished emanator surface 4. The emanator 3 is formed from a porous ceramic material. A conduit in the form of a vertical dip tube 5 is provided having its upper end in communication with the emanating surface 4 and its lower end terminating slightly above the base portion 2 of the vessel.

The vessel is partly filled with a liquid fragrance composition 6 so that the upper portion 7 of the vessel contains air. The amount of liquid fragrance in the vessel is such that the lower end of the dip tube 5 is submerged.

At constant pressure, which is essentially what occurs in a device of less than about 150 mm in height, the volume coefficient of expansion of air is 0.35% per degree C at 10° C. Thus, suitable ranges for the dimensions of the component parts of the device can be calculated depending upon variables such as the operational lifetime of the device, the amount of liquid expelled, whether the fragrance is diluted in some way, etc. The overall volume of the closed vessel may be about 2 milliliters to about 2 liters, with a preferred range of about 10 ml to about 200 ml, with the liquid volume calculated according to the nature of the fragrance composition, the required working life, the expected temperature range, etc. The diameter of the dip tube would typically lie in a range of about 1.0 to about 5.0 mm.

Figure 2:
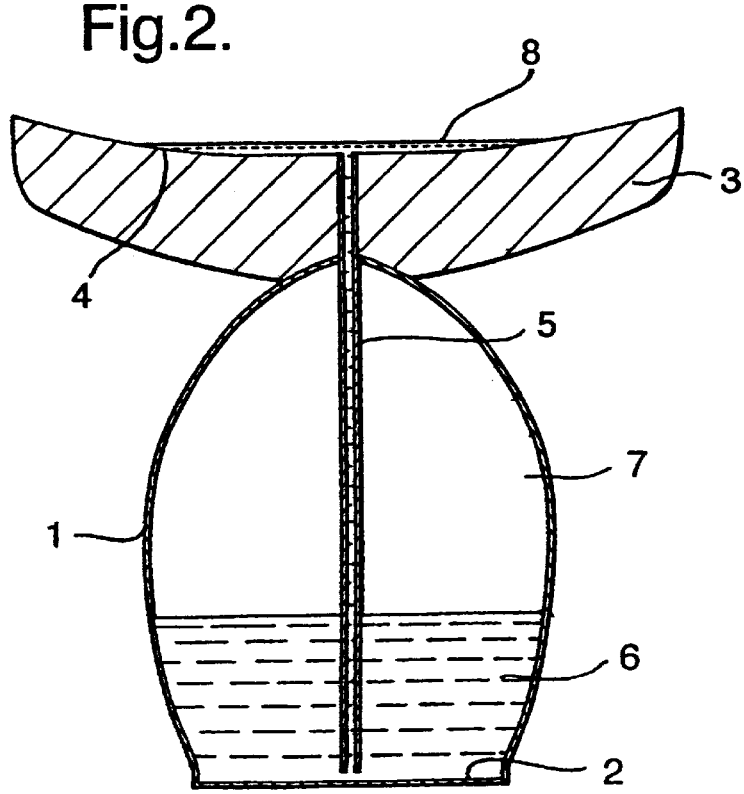
FIG. 2 is a cross-sectional view of the device of FIG. 1 during the elevated temperature portion of a daily cycle.

As shown in FIG. 2, a slight expansion of the air in the upper portion 7 of the vessel has forced the liquid fragrance composition to rise slightly up the dip tube 5. As the temperature rises during the course of the day, the expansion of the air in the vessel increases. The relative volumes of the vessel 1 and the dip tube 5 are such that the expansion of the air causes liquid fragrance composition 6 to rise up the dip tube 5 and form a pool 8 on the surface 4 of the emanator 3. The liquid pool 8 becomes absorbed into the emanator. The fragrance evaporates from this pool and freshens the air.

As the temperature falls during the night, the air in the vessel 1 contracts and the liquid fragrance composition in dip tube 5 is drawn back into the vessel 1. Continued contraction of the air then draws additional air from the atmosphere into the vessel via dip tube 5 to replace the expelled liquid fragrance composition, because of the relationship between the volume of the vessel 1 and the volume of the dip tub 5. On each successive temperature cycle, fresh fragrance is delivered to the emanator, from where it evaporates into the air.

With successive introductions of atmospheric air into the vessel, for a given range of temperature cycling, the absolute volume expansion increases with successive temperature cycles. As a result, an increased amount of liquid fragrance composition is fed to the emanator every 24 hours, with a corresponding increase in fragrance strength in contrast to conventional slow release air freshening devices where the fragrance strength gradually decreases with time.

The device of the present invention is particularly suitable for use in rooms where there is a diurnal temperature variation, so that the emanator is charged with fresh fragrance composition each day.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A fragrance emanating device for freshening atmospheric air, the device comprising:
    (i) a closed container for accommodating a liquid fragrance composition in an interior of the container,
    (ii) an emanator having a surface open to ambient air for evaporation of the liquid fragrance composition, and
    (iii) a conduit linking the interior of the container and the emanator surface, the conduit comprising a dip tube vertically disposed within the container and extending from the emanator surface to a position near a bottom of the container, the dip tube having an upper end in communication with the emanator surface,
    wherein the container is formed such that expansion of air and/or liquid in the container only occurs up the dip tube, and
    wherein the container and the dip tube are so dimensioned that, in use, thermal expansion of air and/or liquid in the container, resulting from an increase in temperature, causes a portion of the fragrance composition to travel along the conduit from the container to the surface of the emanator, and thermal contraction of the air and/or liquid in the container, resulting from a decrease in temperature, causes ambient air to enter the container via the conduit.

2. The device as claimed in claim 1, wherein the emanator has a dished surface.

3. The device as claimed in claim 1, wherein the container is thermally insulated.

4. The device as claimed in claim 1, wherein the container initially contains air with the liquid fragrance composition.

5. The device as claimed in claim 1, wherein the container is initially completely filled with liquid fragrance composition.

6. The device as claimed in claim 1, wherein the emanator comprises a porous material.

7. The device as claimed in claim 6, wherein the porous material is selected from the group consisting of ceramic material, earthenware material, plastic material, paper, cellulose wadding, and finely divided mineral particles.

8. The device as claimed in claim 1, wherein the dip tube has a diameter of about 1.0 to about 5.0 mm.

9. The device as claimed in claim 1, wherein the container has a volume of about 10 to about 200 ml.

10. A method of freshening ambient air, comprising:
    providing a fragrance emanating device comprising:
    (i) a closed container accommodating a liquid fragrance composition in an interior of the container;
    (ii) an emanator having a surface open to ambient air for evaporation of the liquid fragrance composition; and
    (iii) a conduit linking the emanator surface and the liquid fragrance composition in the interior of the container, the conduit comprising a dip tube vertically disposed within the container which extends between the emanator surface and the base of the container, the dip tube having an upper end in communication with the emanator surface, occurred in an atmosphere which is subject to temperature change, wherein the container is formed such that thermal expansion of the air and/or liquid in the container, resulting from an increase in temperature, causes a portion of the fragrance composition to travel along the conduit from the container to the surface of the emanator, and thermal contraction of the air and/or liquid in the container, resulting from a decrease in temperature, causes ambient air to the enter the container via the conduit.

11. The method as claimed in claim 10, wherein the emanator has a dished surface.

12. The method as claimed in claim 10, wherein the conduit comprises a dip tube vertically disposed within the container and extending from the emanator surface to a position below an upper surface of the liquid fragrance composition.

13. The method as claimed in claim 10, wherein the container is thermally insulated.

14. The method as claimed in claim 10, comprising initially providing air in the container with the liquid fragrance composition.

15. The method as claimed in claim 10, comprising initially filling the container completely with the liquid fragrance composition.

16. The method as claimed in claim 10, wherein the emanator comprises a porous material.

17. The method as claimed in claim 16, wherein the porous material is selected from the group consisting of ceramic material, earthenware material, plastic material, paper, cellulose wadding, and finely divided mineral particles.

18. The method as claimed in claim 10, wherein the conduit has a diameter of about 1.0 to about 5.0 mm.

19. The method as claimed in claim 10, wherein the container has a volume of about 10 to about 200 ml.

* * * * *